United States Patent [19]

Stubbs

[11] Patent Number: 5,052,410

[45] Date of Patent: Oct. 1, 1991

[54] DEVICE FOR CONTROLLING EATING AND SMOKING HABITS

[76] Inventor: James M. Stubbs, 112 N. Lawrence St., Rockingham, N.C. 28379

[21] Appl. No.: 602,656

[22] Filed: Oct. 24, 1990

[51] Int. Cl.⁵ .............................................. A61F 5/00
[52] U.S. Cl. ..................................... 128/859; 128/860
[58] Field of Search ............................... 126/859-862

[56] References Cited

U.S. PATENT DOCUMENTS

| | | | |
|---|---|---|---|
| 2,142,614 | 1/1939 | Mitchell | 128/859 |
| 2,192,558 | 3/1940 | Poindexter | 128/861 |
| 3,187,746 | 6/1965 | Gerber | 128/859 |
| 3,224,442 | 12/1965 | Stubbs | 128/859 |
| 3,295,519 | 1/1967 | Gerber | 128/860 |
| 3,584,620 | 6/1971 | Hale | 128/859 |
| 3,587,590 | 6/1971 | Hastings | 606/234 |
| 3,818,906 | 6/1974 | Stubbs | 128/860 |
| 4,718,662 | 1/1988 | North | 128/860 |
| 4,955,393 | 9/1990 | Adell | 128/859 |

Primary Examiner—Mickey Yu
Assistant Examiner—Michael Brown
Attorney, Agent, or Firm—Dowell & Dowell

[57] ABSTRACT

Apparatus for reducing the craving for food and tobacco smoke including a flexible resilient member having a central portion with an intermediate portion inclined upwardly received between the lower lip and teeth and a pair of outwardly extending apertured side portions received between the user's cheeks and the teeth at the sides of the mouth. The central portion has a tab which may be flipped back and forth by the tongue.

3 Claims, 1 Drawing Sheet

DEVICE FOR CONTROLLING EATING AND SMOKING HABITS

BACKGROUND OF THE INVENTION

Cross-reference to Related Patents

This is an improvement on my invention described in patent 3,818,906.

Field of the Invention

This invention relates generally to the overall well being and health of an individual and relates particularly to apparatus for controlling or satiating the craving experienced by many which is satisfied orally by eating and smoking.

Description of the Prior Art

It is recognized by some authorities that many persons overeat, drink and smoke for the purpose of meeting a psychological need. In the past efforts for overcoming the psychological need have been directed to the use of will power with little effort being directed toward apparatus to assist in overcoming the need.

Various devices for use in the mouth have been known. My earlier U.S. Pat. Nos. 3,224,442 and 3,818,906 disclose devices which are positioned along the cheeks and have a tab which may be flipped with the tongue.

The U.S. Pat. to Gerber No. 3,187,746 and 3,295,519 disclose mouth exercisers that are held in the mouth for orthodontic purposes.

The U.S. Pat. to Hastings No. 3,587,590 discloses a button-like device of plastic for satisfying a person's need for food and smoking.

The U.S. Pat. to Mitchell No. 2,142,614 discloses a moldable plate having outer rounded ends and a reduced central portion for use by an undertaker as a mouth plate.

The U.S. Pat. to Hale No. 3,584,620 discloses upper and lower resilient bands for use in a person's mouth to puff out the lips and cheeks in order to reduce the appearance of aging.

SUMMARY OF THE INVENTION

This invention is an apparatus received within the oral cavity or mouth of a person to assist in controlling or overcoming the psychological need to eat more than is necessary or to smoke tobacco products. The apparatus includes a flexible member of sheet material of a configuration to be received between the teeth and the cheeks and lower lip and having a portion projecting inwardly into proximity with the tongue.

It is an object of the invention to provide an apparatus which a person can place in his mouth and which causes salivary fluids to flow to help control or satiate the psychological need to overeat or smoke, and which is an improvement on my previous patents.

DESCRIPTION OF THE PREFERRED EMBODIMENT

Figure 1:
FIG. 1 is a perspective illustrating one application of the invention in use.
Figure 2:
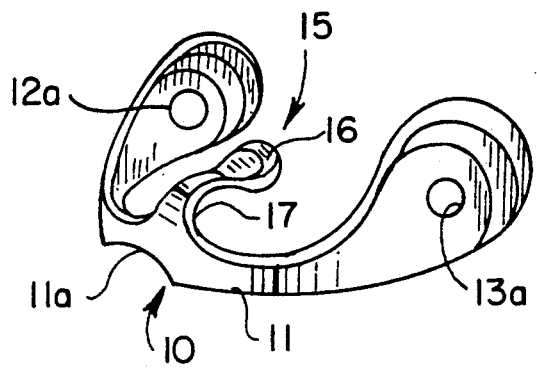
FIG. 2 is an enlarged perspective illustrating the configuration that the device assumes when in use.
Figure 3:
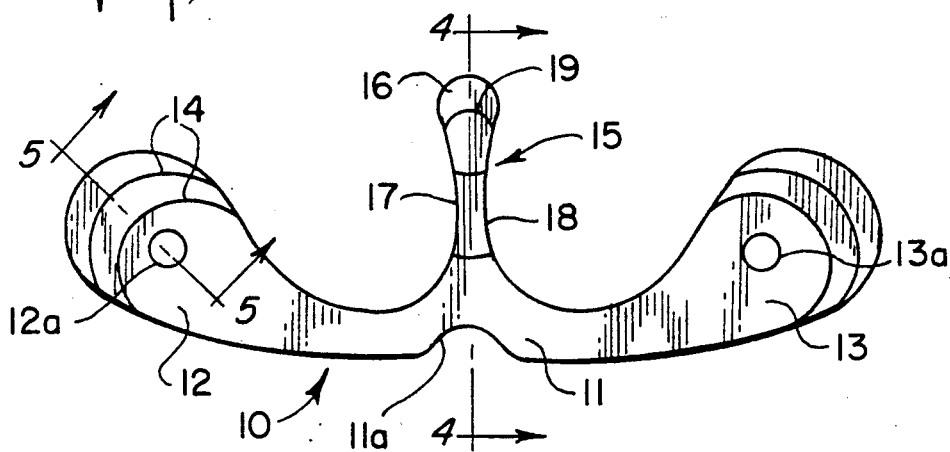
FIG. 3 is a top plan view of the device.
Figure 4:
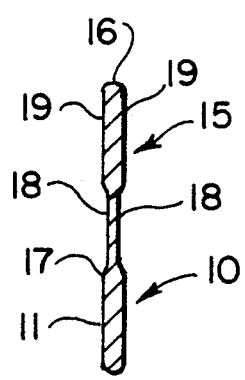
FIG. 4 is an enlarged section on the line 4—4 of FIG. 3.
Figure 5:
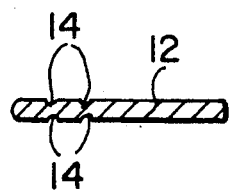
FIG. 5 is an enlarged section on the line 5—5 of FIG. 3.

With further reference to the drawing, a mouthpiece 10 of flexible, resilient, chemically inert material is provided having a relatively thin narrow central portion 11 integrally connected to outwardly extending enlarged side portions or wings 12 and 13. As illustrated best in FIG. 3, the lower edge of the central portion and the lower edges of the side portions 12 and 13 are substantially coextensive in a gentle curve. However, in order to avoid pressure on the frenum membrane connecting the lower lip with the gum, the intermediate portion 11a of the lower edges of the central portion is inclined upwardly in the central region to accommodate the membrane.

The upper edges of the side portions curve upwardly to provide a teardrop shape for the side portions. Each of the side portions 12 and 13 is provided with one or more score lines 14 on at least the front surface thereof and such score lines are used as guide lines for altering the size of the mouthpiece with scissors or other sharp instruments. Furthermore, each of the side portions 12 and 13 is provided with an aperture 12a, 13a in order to facilitate the flow of saliva from the parotid ducts in the cheeks into the mouth, thereby enhancing the functioning of the device.

An upwardly extending tab 15 is integrally formed with the central portion 11 and such tab includes a head 16 connected by a reduced neck 17 to the central portion. In order to facilitate more flexible movement of the tab 15, the neck 17 is provided with relatively wide recesses 18 in both the front and rear surfaces of the neck to provide a portion of reduced thickness and increased flexibility. The head 16 includes at least one score line 19 for use as a guide in reducing the size of the head. The intermediate portion 11a extends into the central portion beneath the tab 15, to a height substantially as high as the upper sides of the portion 11 in order to avoid pressure on the frenum membrane, as stated above.

The entire mouthpiece is molded of one-piece construction and can be molded from rubber or from a thermoplastic synthetic organic polymeric resin such as the acrylics, styrenes and modified styrenes, vinyls, polyethylene and the like which are non-absorbent, flexible, tasteless and chemically inert so that the mouthpiece can remain in the mouth for extended periods of time while the user is awake without irritation or discomfort. It has been found that a molded rubber product marketed by Shell Chemical Company and designated as Kraton 2109 is well suited for this purpose.

In the use of the device, the mouthpiece 10 is curved generally to the configuration of a person's lower jaw and is inserted into the mouth with the central portion 11 located between the lower lip and the lower incisor teeth, while the side portions 12 and 13 extend rearwardly to a position between the cheeks and the molars. The tab 15 extends over the incisors and into proximity with the tongue so that the user can toy with the tab either consciously or unconsciously. Due to the presence of a foreign body within the mouth, a person's salivary glands will excrete saliva which at least partially fills the psychological need to overeat or to smoke tobacco products. The apertures 12a and 13a permit a greater profusion of saliva to pour into the mouth to swallow as the wings 12 and 13 move teasingly against the parotid duct (an opening through which saliva pours from the cheek into the mouth), thus improving the functioning of the device.

I claim:

1. Apparatus for reducing the psychological need of excessive caloric intake, as well as the need for smoking tobacco, comprising a flexible resilient sheet member of substantially chemically inert non-absorbent material, said member having a central portion and a pair of side portions, said side portions having an exterior and an interior, said central portion being of narrow width and of a length to fit between the lower lip and the lower incisor teeth of a user, said side portions being integrally connected to said central portion and having an enlarged substantially teardrop configuration, said side portions adapted to fit between the cheeks and the molar teeth of the lower jaw of the user, and flexible resilient tab means integrally connected to said central portion and extending generally upwardly from the upper edge thereof when said central portion is positioned between the incisor teeth and lower lip of the user and being bendable rearwardly over the lower incisor teeth of the user, said central portion having upper and lower edges, the lower edges inclined upwardly intermediate the ends of said central portion and beneath the connection to said flexible tab means in order to avoid pressure on the user's frenum membrane, and said side portions having openings extending from said interior wall to said exterior wall of said teardrop configuration to facilitate the flow of saliva from the user's cheek duct through said side portions and into the mouth, whereby when said member is inserted into the mouth of the user said tab means may be manipulated both horizontally and vertically by the tongue of the user.

2. The structure of claim 1 in which said tab means has a portion of reduced thickness intermediate its length to facilitate movement of said tab means by the user's tongue.

3. The structure of claim 1 in which each of said side portions and said tab means includes guide lines for facilitating reduction in size of said member.

* * * * *